(12) United States Patent
Noguera Aguilar et al.

(10) Patent No.: US 11,571,240 B2
(45) Date of Patent: Feb. 7, 2023

(54) SURGERY MULTICHANNEL DEVICE

(71) Applicant: SERVIZO GALEGO DE SAÚDE (SERGAS), Santiago de Compostela—a Coruña (ES)

(72) Inventors: José Francisco Noguera Aguilar, Santiago de Compostela—a Coruña (ES); Javier Aguirrezabalaga González, Santiago de Compostela—a Coruña (ES); Alberto Centeno Cortés, Santiago de Compostela—a Coruña (ES)

(73) Assignee: SERVIZO GALEGO DE SAÚDE (SERGAS), Santiago (ES)

( * ) Notice: Subject to any disclaimer, the term of this patent is extended or adjusted under 35 U.S.C. 154(b) by 0 days.

(21) Appl. No.: 16/620,004

(22) PCT Filed: Jun. 6, 2018

(86) PCT No.: PCT/EP2018/064913
§ 371 (c)(1),
(2) Date: Dec. 6, 2019

(87) PCT Pub. No.: WO2018/224557
PCT Pub. Date: Dec. 13, 2018

(65) Prior Publication Data
US 2021/0186557 A1 Jun. 24, 2021

(30) Foreign Application Priority Data
Jun. 7, 2017 (EP) ..................................... 17382349

(51) Int. Cl.
*A61B 17/34* (2006.01)
*A61B 17/00* (2006.01)

(52) U.S. Cl.
CPC ...... *A61B 17/3423* (2013.01); *A61B 17/3462* (2013.01); *A61B 2017/00544* (2013.01); *A61B 2017/00557* (2013.01); *A61B 2017/3466* (2013.01)

(58) Field of Classification Search
CPC ............ A61B 17/3423; A61B 17/3439; A61B 17/3462
See application file for complete search history.

(56) References Cited

U.S. PATENT DOCUMENTS 8,485,970 B2 * 7/2013 Widenhouse ...... A61B 17/0218
600/201
2004/0138684 A1 7/2004 Eton
(Continued)

FOREIGN PATENT DOCUMENTS

EP 2168511 A2 3/2010
WO 2016064617 A1 4/2016

OTHER PUBLICATIONS

International Search Report and Written Opinion for PCT/EP2018/064913 dated Aug. 31, 2018.

*Primary Examiner* — Si Ming Ku
(74) *Attorney, Agent, or Firm* — Thomas | Horstemeyer, LLP

(57) ABSTRACT

The invention provides a pneumatic sealing system device which allows sealing a working channel, a surgery multichannel device comprising a pneumatic sealing system and a method for installing said pneumatic sealing system on a multichannel device. The device is a mentioned instruments simultaneously.

15 Claims, 7 Drawing Sheets

(56) References Cited

U.S. PATENT DOCUMENTS

| | | | | |
|---|---|---|---|---|
| 2005/0267419 A1* | 12/2005 | Smith | ............... | A61B 17/3423 604/256 |
| 2007/0270866 A1* | 11/2007 | von Jako | ........... | A61B 17/3423 606/86 R |
| 2012/0157779 A1* | 6/2012 | Fischvogt | .......... | A61B 17/0293 600/207 |
| 2017/0095269 A1* | 4/2017 | Reid | ................. | A61B 17/3423 |

* cited by examiner

SURGERY MULTICHANNEL DEVICE

CROSS-REFERENCE TO RELATED APPLICATIONS

This application is the 35 U.S.C. § 371 national stage application of PCT Application No. PCT/EP2018/064913, filed Jun. 6, 2018, which claims priority to and the benefit of European Patent Application EP17382349.3 titled "SURGERY MUTLICHANNEL DEVICE" filed Jun. 7, 2017, the entire disclosures of which are incorporated herein by reference.

TECHNICAL FIELD OF THE INVENTION

The present invention belongs to the field of medical devices, in particular to the field of devices for surgery with the possibility of using a flexible endoscope in parallel with rigid instruments by means of a universal platform. More specifically, the invention is of special application in the single incision surgeries, particularly abdominopelvic surgery.

BACKGROUND OF THE INVENTION

Minimally invasive surgery is being developed in order to achieve surgery which is able to avoid or minimize as much as possible the main problems of laparoscopic surgery on the patient, such as surgical wound infection, adhesions, post-operational pain, ventral hernias, etc.

According to this target, NOTES (Natural Orifice Transluminal Endoscopic Surgery) has been developed to produce a minor trauma to the abdominopelvic wall. This particular surgery combines laparoscopic surgery for reproducing the intraperitoneal surgery technique along with the knowledge on flexible endoscope to access the abdominal cavity through natural orifices as the mouth, the vagina, the anus or the urethra. Until now, the transvaginal approach has been the most successful approach of this surgery since NOTES development started.

However, the development of this type of surgery has been rather uneven, and present several drawbacks such as the way to open and close the gastrostomy, the impossibility to work in parallel with additional laparoscopic instruments or the difficulty to act effectively and safely if complications arise during the surgery.

Particularly, using a flexible endoscope through a device for rigid instruments implies additional complications to those already derived from a surgery.

SUMMARY OF THE INVENTION

The present invention provides a solution for the aforementioned problem of working in parallel with flexible endoscopes while performing the surgery by means of rigid laparoscopic instruments or optics, thus achieving a "fusion surgery", known as "Flexible Single Incision Surgery (FSIS)", through a device which is able to combine the mentioned instruments simultaneously. Thus, rigid and flexible instruments are combined, allowing the mentioned "fusion surgery" by using this flexible platform for surgery, particularly endoscopic surgery.

Particularly, the present invention provides of a new single-port multichannel surgical device adapted to flexible endoscopic platforms which makes possible an operation using both rigid instruments and flexible endoscopy platforms. Said flexible endoscopy platforms are sealed by means of another inventive aspect of the invention, a pneumatic sealing system.

Therefore, by means of the present invention, flexible endoscopes through a conventional trocar or device for single incision surgery is allowed, in opposition with nowadays trocars and devices, which do not allow working with flexible endoscopes due to problems with the endoscope's movements and the possibility of damaging it in its flexible part.

Thus, the present invention presents a pneumatic sealing system device according to claim 1, a surgery multichannel device according to claim 6 and a method for installing a pneumatic sealing system on a multichannel device according to claim 14. In dependent claims, preferred embodiments of the invention are defined.

In a first inventive aspect, the invention provides a pneumatic sealing system suitable for being installed in a working channel of a surgery device comprising:
   an inflatable pad inflatable with a fluid, such inflatable pad being configured for exerting pressure on an external element when inflated,
   a main body wherein the inflatable pad is located, the main body comprising:
      a first surface,
      a second surface opposite the first surface,
      an inner passage,
      a fluid distribution system for inflating said inflatable pad through the inner passage,
      a first sealing portion and a second sealing portion, said sealing portions located on the first surface and the second surface respectively of the main body, both sealing portions sealing the inflatable pad, and
      at least one fixing member for fixing the inflatable pad to the main body.

Throughout this entire document, "channel" will be understood as a path wherein a surgical instrument, such as endoscopes, instruments or optics, either flexible or rigid, are introduced in order to be utilized during a surgery.

Thus, a "working channel" provides of a channel wherein an instrument can be handled, being said instrument either flexible endoscopes or rigid optics. In a particular embodiment, such instrument is a flexible endoscope.

Advantageously, the present pneumatic sealing system allows sealing a channel housing any elongated instrument during a surgery, in order to avoid an air leak of the cavity through the channel. Said instrument may be a flexible endoscope or any other instrument, rigid or flexible.

Particularly, the sealing system allows minimizing losses of the virtual space (pneumoperitoneum, pneumorectum or pneumovagina) when using a flexible endoscope during a FSIS surgery. Said sealing system is installed in the mentioned surgery device, avoiding the need of an additional single-port device for the flexible endoscope during the surgery.

In a particular embodiment, the present pneumatic sealing system is installed inside the working channel of the surgery device.

In a particular embodiment, the instrument sealed is a rounded-section instrument, preferably with an external diameter between 3-20 mm, more particularly between 5-20 mm and more preferably between 5-18 mm.

The inflatable pad of the sealing system is an element which swells when a fluid is introduced inside it, and produces the sealing of the working channel by applying pressure to the instrument located inside said working channel, by means of the perimeter of the swelled inflatable pad.

Particularly, the inflatable pad is shaped with at least three swelling lobes when inflated which allow the exertion of pressure on the instrument.

In a particular embodiment, the fluid for inflating the inflatable pad is air, $CO_2$, water or a saline solution. In a preferred embodiment the fluid is air.

Said inflatable pad is made of a material with adequate elasticity and resistance properties which allow its swelling with the fluid and the restauration of its shape when said fluid is removed, and which also allows exerting pressure on the instrument without tearing.

In a particular embodiment, the inflatable pad is made of a polymer, particularly natural rubber latex, more particularly natural rubber latex with bismuth oxide, such as the material present in surgical gloves.

The main body of the sealing system is a piece which distributes, by means of the fluid distribution system, the mentioned fluid, particularly air, entering the sealing system into the inflatable pad in order to inflate it.

The inflatable pad is placed between the first and second surface of the main body such that the inner passage allows the entry of external fluid from the fluid distribution system into the sealing system for inflating the inflatable pad.

In a particular embodiment, the main body is made of synthetic polyamide.

The first and second sealing portions allow sealing the inflatable pad when mounted in the main body of the sealing system. Said sealing portions help both locating the inflatable pad in the main body, as well as separating the whole inflatable pad from the outer environment. This further achieves the prevention of any fluid leak in the sealing system, particularly any air leak.

In a particular embodiment, the first and second sealing portions are manufactured with synthetic polyamide.

The at least one fixing member fixes the inflatable pad in the adequate position of the main body, also allowing the first and second sealing portions to be placed in the right position, thus maintaining the mounted configuration of the sealing system.

Additionally, the at least one fixing member ensures that the inflatable pad is completely watertight and that no fluid leak is produced in the sealing system.

In a particular embodiment, the at least one fixing member is an O-ring, more particularly made of rubber, for example 70NBR.

In a particular embodiment, the sealing system further comprises a perimeter recess along the inner passage and the fluid distribution system comprises:
at least one fluid inlet, and
at least one fluid outlet,
wherein the fluid for inflating the inflatable pad flows from the inlet through the perimeter recess and enters the inflatable pad through the outlet.

Advantageously, the inner passage provides of a path for the external fluid to flow through the inner passage of the main body and into the inflatable pad, being the inflation quicker.

Thus, the path followed by the flow of fluid is entering through the at least one fluid inlet, flowing through the inner passage and exiting through the at least one fluid outlet into the inflatable pad. In a particular embodiment, said fluid is air.

The perimeter recess facilitates the fluid, both gas and liquid, distribution and achieves the same pressure exerted by the inflatable pad on the instrument.

Each fluid outlet corresponds with one of the swelling lobes created in the inflatable pad.

In a particular embodiment, the fluid is air and there are three air outlets located in three equidistant points of the main body, advantageously producing a homogenous swelling of the inflatable pad. Each of the air outlets corresponds with a swelling lobe of the inflatable pad.

In a particular embodiment, the fluid distribution system of the sealing system further comprises a luer-lock connection for attaching a 3-way valve.

This advantageously allows the inflation of the inflatable pad with the fluid by means of syringes or a inflating mechanical system.

In a particular embodiment, the inflatable pad is configured by at least three swelling lobes when inflated which surround the external element, namely the instrument.

The configuration with three or four swelling lobes provides a more homogeneous distribution of the pressure exerted by the inflatable pad on the instrument, as well as a better surrounding of the inflatable pad around the instrument, thus maintaining a satisfactory position of said instrument.

In a second inventive aspect, the invention provides a surgery multichannel device suitable for single incision surgery or natural orifices endoscopic surgery comprising a main working channel, wherein the device further comprises a pneumatic sealing system according to the first inventive aspect, which is installed in the main working channel of the mentioned device.

Advantageously, the device is a surgical multichannel device which allows performing single incision surgery or natural orifices endoscopic surgery with rigid instruments and flexible endoscope in combination. A surgical procedure with rigid instruments (rigid optics and laparoscopic instruments) is possible, but the present device allows the possibility of using a flexible endoscope without the problems of damaging it and without losing the cavity pressure where the surgery is being performed by a leak, particularly a $CO_2$ leak.

Additionally, the device allows a complete freedom of movements for the flexible endoscope without leaks of $CO_2$, said $CO_2$ being used for the creation of the virtual space (pneumoperitoneum, pneumorectum or pneumovagina) necessary for the surgery.

In a particular embodiment, the device is a FSIS device which allows the introduction of a flexible endoscope through a very short working channel, with a short but efficient pneumatic seal. Advantageously, said FSIS device is the only one allowing the simultaneous use of a flexible endoscope within the device where the surgery instruments are introduced.

In a particular embodiment, the device has a funnel shape and can be made mainly of synthetic polyamide. The funnel-shaped device thus comprises a neck on one of its ends.

In a particular embodiment, the main working channel houses a flexible endoscope or rigid optic, which allows a good and wide endoscope/optic mobilization without leaks in $CO_2$ of the cavity (abdomen, rectum or vagina) wherein the surgery is being performed, and also avoids any damage of the mentioned flexible endoscope/rigid optic.

In a particular embodiment, the main working channel houses rounded-section instruments.

Advantageously, the inflatable pad of the sealing system of the device allows a better housing of the rounded-sectioned instruments by means of the swelling performed.

Thus, a better sealing is achieved which avoids leaks of $CO_2$ from the cavity (abdomen, rectum or vagina).

Consequently, a universal platform for a single-incision surgery through abdominal, rectal or vaginal access both for surgeons and gastroenterologists is obtained.

In a particular embodiment, the device further comprises:
a cover,
at least one secondary working channel,
at least one air input, and
retention means
wherein the main working channel and the at least one secondary working channel are located in the cover of the device.

The secondary working channel allows using more instruments (rigid or flexible) in addition to the one used in the main working channel, particularly a flexible endoscope. Said instruments are the ones performing the surgery.

In a particular embodiment, the main working channel is located in the cover of the device in parallel with the at least one secondary working channel.

The at least one air input allows the creation of a space for working in the place of the surgery, namely the abdomen, rectum or vagina. Said at least one air input introduces $CO_2$ inside the cavity, thus creating the mentioned space.

In a particular embodiment, the at least one air input of the device comprises a luer-lock system for connecting a pump. Said pump is in charge of maintaining the pneumoperitoneum, pneumorectum or pneumovagina pressure.

In a particular embodiment, the luer-lock system of the mentioned $CO_2$ input is located on one side of the cover.

The retention means allow maintaining the device in its correct place without its extrusion, that is, without an accidental movement of the device during the surgery which causes the displacement of the mentioned device from its adequate position.

In a particular embodiment, said retention means comprise a circular fin in the neck of the device, located at the bottom of said device, which allows positioning the mentioned device at the beginning of the surgery.

In a particular embodiment, the retention means further comprise three fixing fins which allow fixing the cover to the skin of the patient by means of sutures. The fixation to the body is thus stronger so that the device does not vary its position during the surgery, consequently the instrument housed inside the main or secondary working channels are stable. Thus, the combination of the circular fin and the fixing fins maintains the device in its correct position during the surgery.

In a particular embodiment, the fins have been designed with central holes which allow the mentioned suture to the patient.

In a particular embodiment, the three fins are equidistant at $120^2$. Said configuration of the retention allows a more reliable distribution of the retention to the body.

In a particular embodiment, the at least one secondary working channel comprises a trocar attached to it and is configured for housing a rigid instrument. Said trocar may be a commercial trocar.

Advantageously, the trocar allows the mobility of the instruments housed inside which access the body through the mentioned secondary working channel.

In a particular embodiment, the inner part of the cover comprises a retention system which avoids the extraction of the trocar. This provides of a security system for the trocar and thus for the instrument housed inside so that the device is stable during its functioning.

In a particular embodiment, the at least one secondary working channel comprises a flexible gel for housing and retaining the trocar.

Particularly, said gel is a flexible silicone gel wherein the trocar is fixed as it is embedded. This achieves a good mobility for the trocar and therefore a correct functionality of the instrument housed herein, allowing freedom of movements to the straight laparoscopic instruments.

In a particular embodiment, the trocar is directly attached to the cover by means of cyanoacrylate and further comprises a spherical ball joint that fulfills the mobility of the housed instrument.

In a particular embodiment, the device comprises two secondary working channels wherein the central axis of both is coincident on one end of said device.

Advantageously, this offers a broad movement of the housed instruments only limited by the wide of the device. The trocars are placed with a certain separation between them in order to facilitate their combined use, for example during an endoscopic surgery.

In a particular embodiment, wherein the device is funnel-shaped, the central axis of the two trocars is coincident in the central point of the neck of said device.

In a particular embodiment, the trocar of the secondary working channel allows housing an instrument of a diameter ranged between 2-20 mm, particularly between 2-15 mm and more particularly between 5-12 mm.

In a particular embodiment, a secondary working channel comprises a trocar of a diameter of 5 mm and a secondary working channel comprises a trocar with a diameter ranged between 5-12 mm. Both trocars are, in a particular embodiment, commercial.

The instruments housed in the mentioned trocars of the secondary working channels may be 5 to 12 mm laparoscopic instruments, in addition to the flexible instruments/endoscopes introduced by the main working channel.

In a third inventive aspect, the invention provides a method for installing a pneumatic sealing system according to the first inventive aspect in a device according to the second inventive aspect, the method comprising the steps:
a) fixing the inflatable pad to the main body by means of the at least one fixing member,
b) adding sealant on the mounting surfaces of the main body and the first and second sealing portions,
c) locating the first sealing portion and the second sealing portion along with the sealant on the first surface and the second surface of the main body,
d) compressing the inflatable pad, main body, first and second sealing portions and the at least one fixing member together by means of fixing means,
e) inserting the mounted pneumatic sealing system from step d) into the main working channel of the device.

Advantageously, this allows obtaining a device as the second inventive aspect in order to perform surgeries combining the use of flexible and rigid instruments.

In a particular embodiment, step e) comprises resting a portion of the mounted pneumatic sealing system on the cover of the device.

This allows a more stable configuration of the device according to the second inventive aspect when being in use.

In a fourth inventive aspect, the invention provides the use of a device according to the second inventive aspect for surgery combining rigid or flexible instruments and flexible endoscopes.

Therefore, by means of the mentioned device according to the second inventive aspect, both rigid laparoscopic instruments and flexible endoscopes can be used simultaneously during a surgery, particularly a FSIS surgery.

When performing said surgery, a device according to the second inventive aspect is introduced in the provided access, namely a cavity (abdomen, rectum or vagina), by means of a single incision, thus remaining the neck of said device inside the cavity.

The device is then fixed to the patient by means of the retention means, fixing fins in a preferred embodiment which allow suturing the device to the skin of the patient. The flexible endoscope is then introduced in the main working channel, and the pneumatic sealing system according to the first inventive aspect is activated, the inflatable pad thus inflated.

$CO_2$ is then insufflated through the surgery device, particularly through the air input, inside the aforementioned cavity, in order to create a pneumoperitoneum, pneumorectum or pneumovagina pressure inside said cavity.

When the adequate space is created, the flexible endoscope is located in a correct position and surgery instruments, particularly rigid laparoscopic instruments, are introduced through the at least one secondary working channel, depending on the nature of the surgery. The flexible endoscope thus provides with both light and optics which allow the user of the device to perform the surgery.

Additionally, the flexible endoscope provides of additional working channels, namely tertiary working channels, which allow the introduction of additional instruments inside the cavity amongst the at least one secondary channel.

All the features described in this specification (including the claims, description and drawings) and/or all the steps of the described method can be combined in any combination, with the exception of combinations of such mutually exclusive features and/or steps.

DESCRIPTION OF THE DRAWINGS

These and other characteristics and advantages of the invention will become clearly understood in view of the detailed description of the invention which becomes apparent from a preferred embodiment of the invention, given just as an example and not being limited thereto, with reference to the drawings.

DETAILED DESCRIPTION OF THE INVENTION

Figure 1:
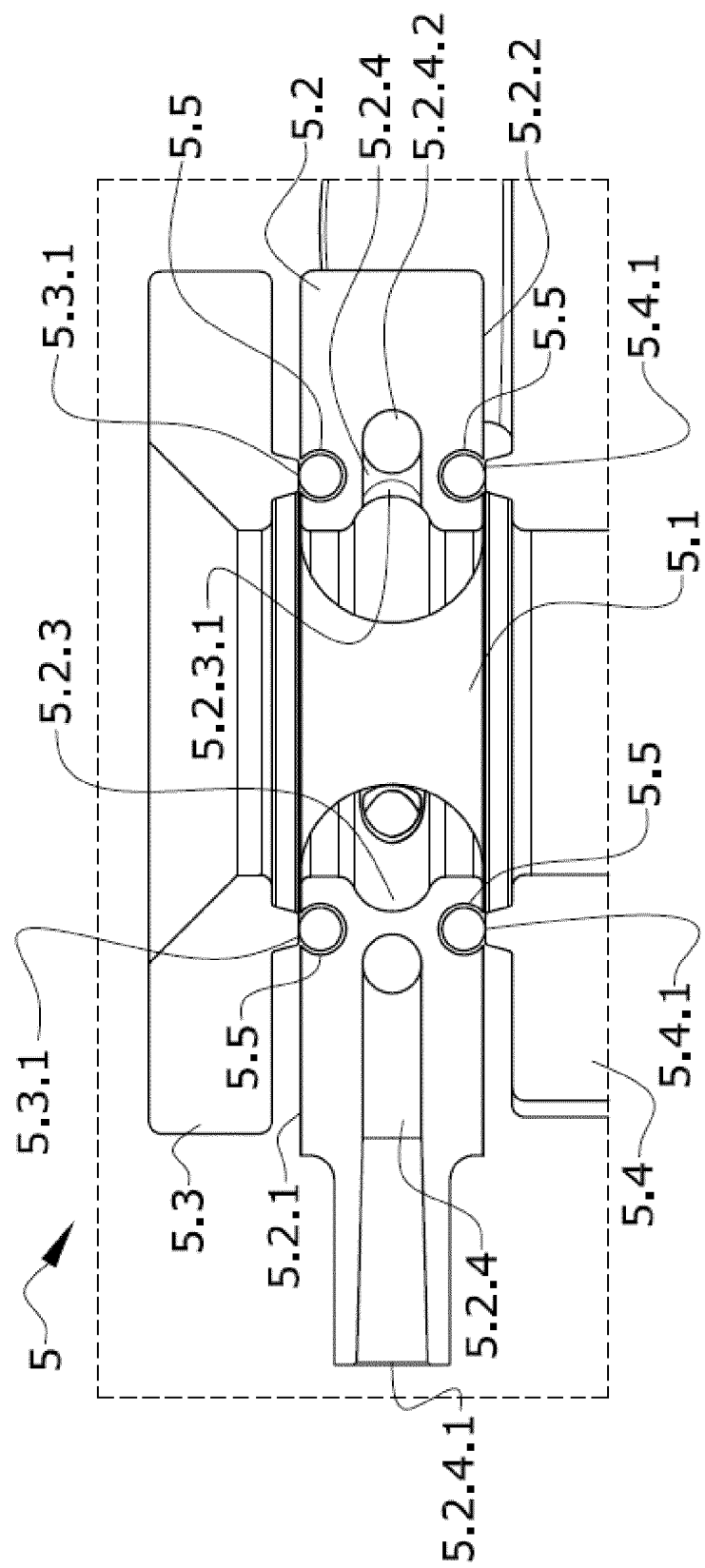
FIG. 1 This figure shows a cross-section of the configuration of a first example of a sealing system.

The present invention describes an example of a sealing system (5) as the one shown in FIG. 1.

In this figure, a cross-section view according to a longitudinal plane of a mounted sealing system (5) is shown. This system (5) comprises a main body (5.2), wherein the first surface (5.2.1) is the one located on the top of the mentioned figure, whereas the second surface (5.2.2) is the surface opposite the first surface (5.2.1) thus located in the bottom of the mentioned figure.

As shown, the main body (5.2) comprises a through-hole which is mechanized in the center. Said through-hole houses the inflatable pad (5.1), being the ends of the mentioned inflatable pad (5.1) supported on the first surface (5.2.1) and on the second surface (5.2.2) respectively.

The inflatable pad (5.1) is swelled inside the through-hole of the main body (5.2), thus occupying this free space. In this example, the inflatable pad (5.1) is made of latex such as the one present in a surgery glove.

On top of the first surface (5.2.1) is located a first sealing portion (5.3). The first sealing portion (5.3) comprises tabs (5.3.1) which are supported on the first surface (5.2.1) of the main body (5.2). Additionally, said tabs (5.3.1) are fixed by means of the fixing member (5.5), which is an O-ring in this example.

Analogously, the second sealing portion (5.4) is located on the second surface (5.2.2), also supported by means of tabs (5.4.1) and fixed by means of another O-ring (5.5).

The mentioned through-hole of the main body (5.2) coincides with the through-hole of the first (5.3) and second (5.4) sealing portions.

The main body (5.2) also comprises a unique cylindrical air distribution system (5.2.4) wherein the end is threaded. The air inlet (5.2.4.1) allows a flow of air to enter the sealing system (5) through the inner passage (5.2.3), exiting through the air outlets (5.2.4.2). Additionally, the perimeter recess (5.2.3.1) performed in the inner passage (5.2.3) of the main body (5.2) allows a better entry and distribution of the air flowing inside the inflatable pad (5.1).

For obtaining the system (5) of FIG. 1, the inflatable pad (5.1) is fixed to the main body (5.2) by means of the O-rings (5.5), thus the ends of the inflatable pad (5.1) being supported on the first (5.2.1) and second (5.2.2) surfaces.

After this, sealant (not shown) is added on the first (5.2.1) and second (5.2.2) surfaces of the main body (5.2), being those the mounting surfaces of said main body (5.2) as well as on the first (5.3) and second (5.4) sealing portions.

Said first (5.3) and second (5.4) sealing portions are located with the added sealant (not shown) on the first (5.2.1) and second (5.2.2) surfaces of the main body (5.2), which also have sealant.

Figure 3:
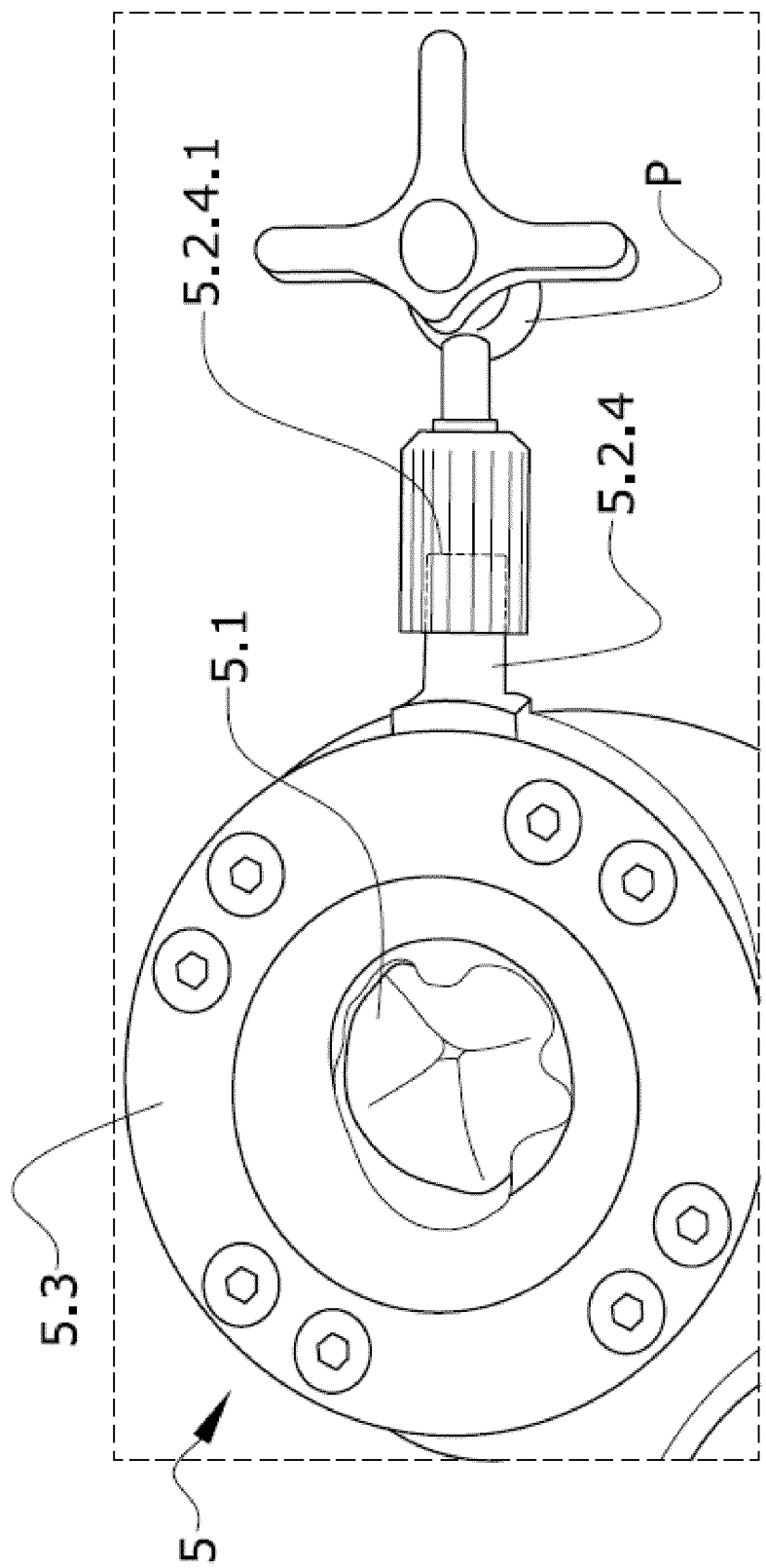
FIG. 3 This figure shows a plan view of the same example of a sealing system of FIG. 1 when mounted.

In order to fix the totality of the parts, namely the inflatable pad (5.1), main body (5.2), first (5.3) and second (5.4) sealing portions and the at least O-rings together, screws are used as shown in FIG. 3, compressing the mentioned parts (5.1, 5.2, 5.3, 5.4).

Figure 2A:
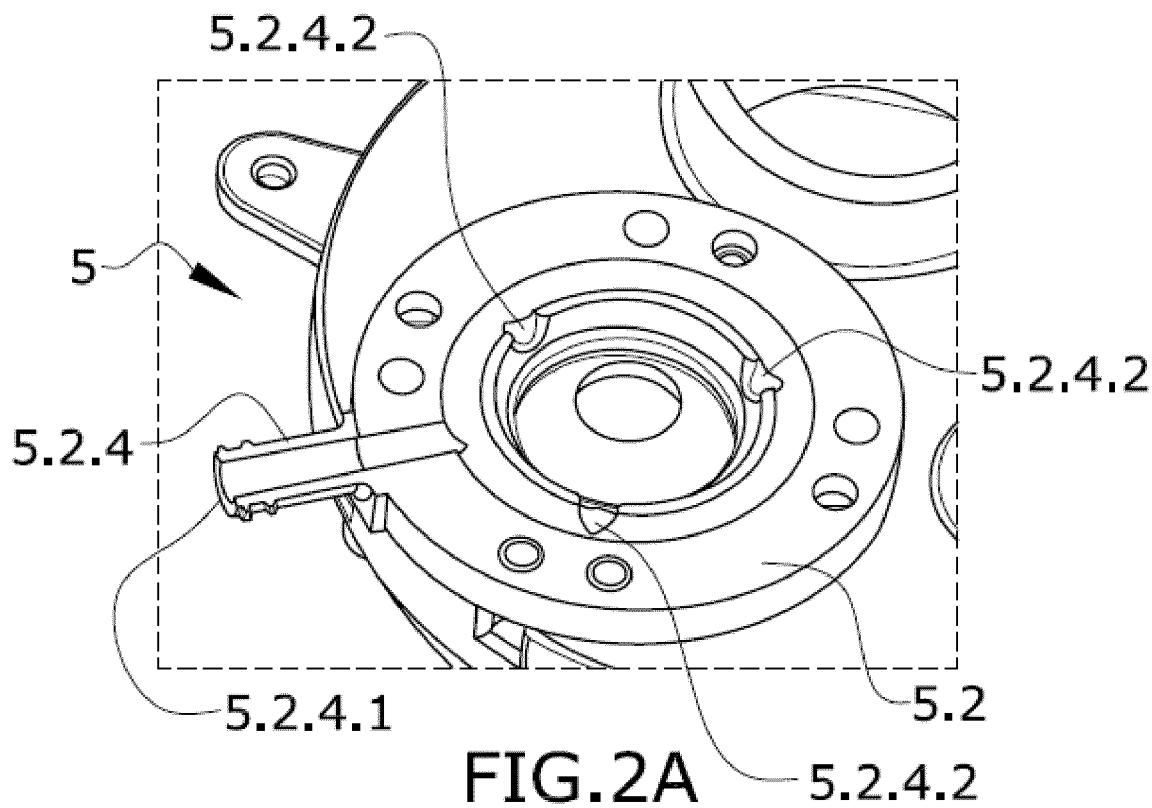
FIGS. 2A-2B These figures show a detail of the same example of a sealing system of FIG. 1.
Figure 2B:
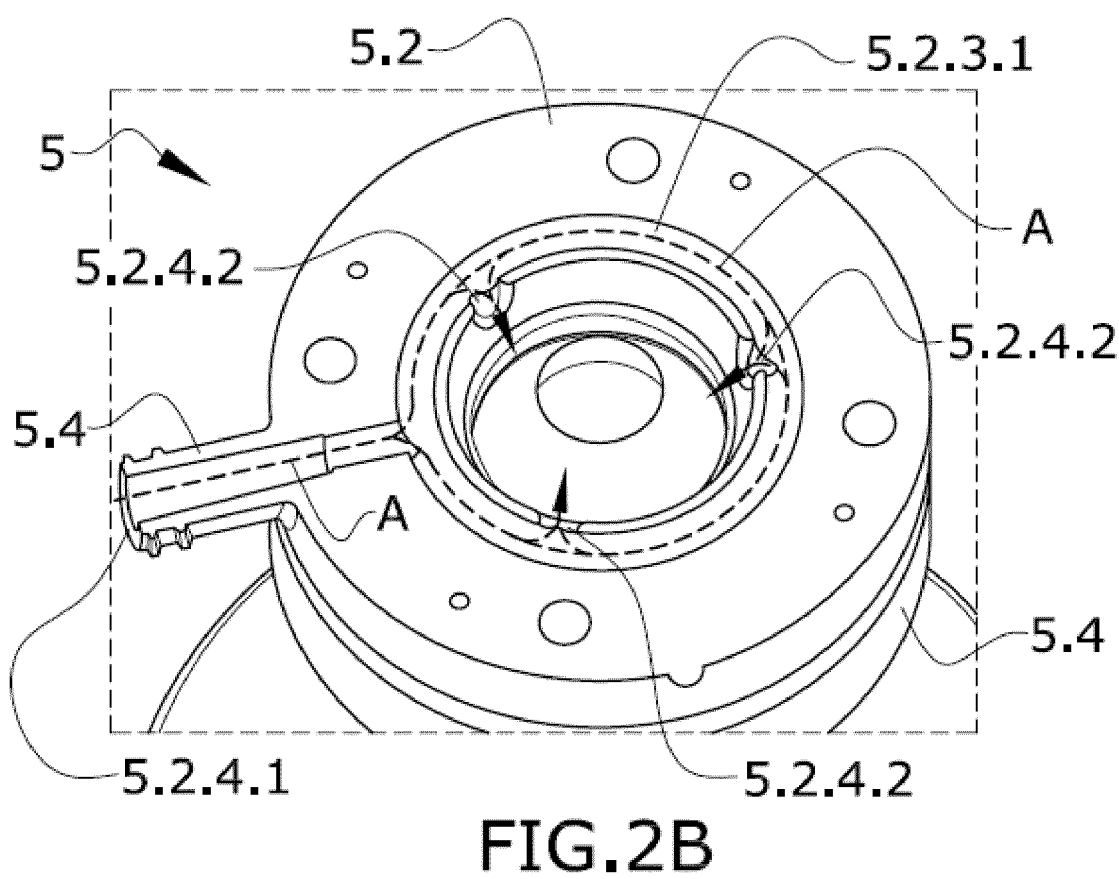

FIGS. 2A and 2B show the same sealing system (5) of FIG. 1, although now plan views of a transversal cross-section of the system (5) are shown.

In FIG. 2A, there is an air inlet (5.2.4.1) and three air outlets (5.2.4.2), located in a circumference and each one (5.2.4.2) separated by 120° from the other two air outlets (5.2.4.2).

Said three air outlets (5.2.4.2) are in fluid communication with the perimeter recess (5.2.3.1) of the main body (5.2) thus allowing the flow of air into the inflatable pad (5.1).

Said flow of air (A) is shown in FIG. 2B by means of arrows which flow from the air inlet (5.2.4.1) of the air distribution system (5.2.4), through the inner passage (5.2.3) by means of the perimeter recess (5.2.3.1) and into the inflatable pad (5.1) through the three circular air outlets (5.2.4.2).

Holes performed in the main body (5.2) shown in both FIGS. 2A and 2B are threaded holes which allow the mounting of a screw for fixing the parts of the sealing system (5).

FIG. 3 shows a plan view of the sealing system (5) already mounted with a pump (P) through a three-way valve. Said pump (P) is mounted by means of a threaded connection, namely a luer-lock connection, to the air inlet (5.2.4.1) of the air distribution system (5.2.4).

It can also be observed in the present figure how the inflatable pad (5.1) is swelled, thus forming four swelling lobes leaving a space in the middle of them which allows surrounding an external element, namely a surgery instrument, which passes through the through-hole of the sealing system (5). The surgery instrument is pneumatically sealed from the external environment by means of the inflatable pad (5.1) operated in the sealing system (5).

The first sealing portion (5.3) as shown in FIG. 3 is fixed to the main body (5.2) by means of screws.

Figure 4:
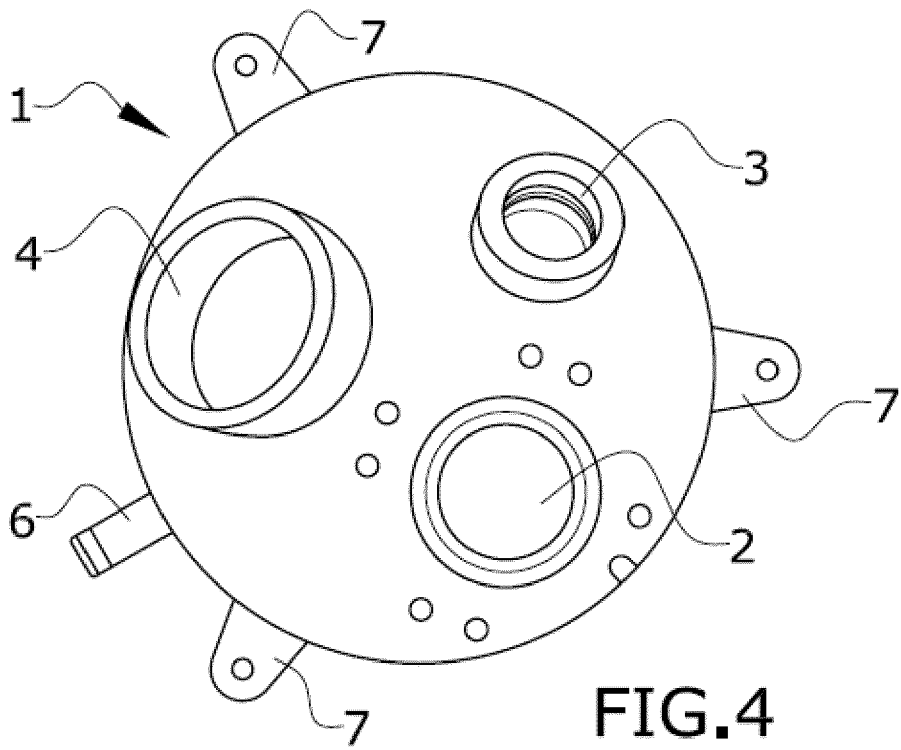
FIG. 4 This figure shows a plan view of a first example of the surgery device.

FIG. 4 shows a top view of a surgery multichannel device (1) which has not yet been mounted with additional elements such as the pneumatic sealing system (5).

Thus, the body (1.2) of the device (1) can be observed wherein a main working channel (2) and two secondary working channels (3, 4) are configured through the mentioned body. It can be observed that one of the secondary working channels (4) is wider that the other (3).

The main working channel (2) has holes around the perimeter of its diameter wherein the sealing system (5) is fixed.

Additionally, the device (1) comprises a $CO_2$ input (6) to the cavity in order to create an space wherein a surgery can be performed, and three fixing fins (7) with central holes which can be sutured to the body. The three fins are equidistant at 120° one from the other.

Figure 5:
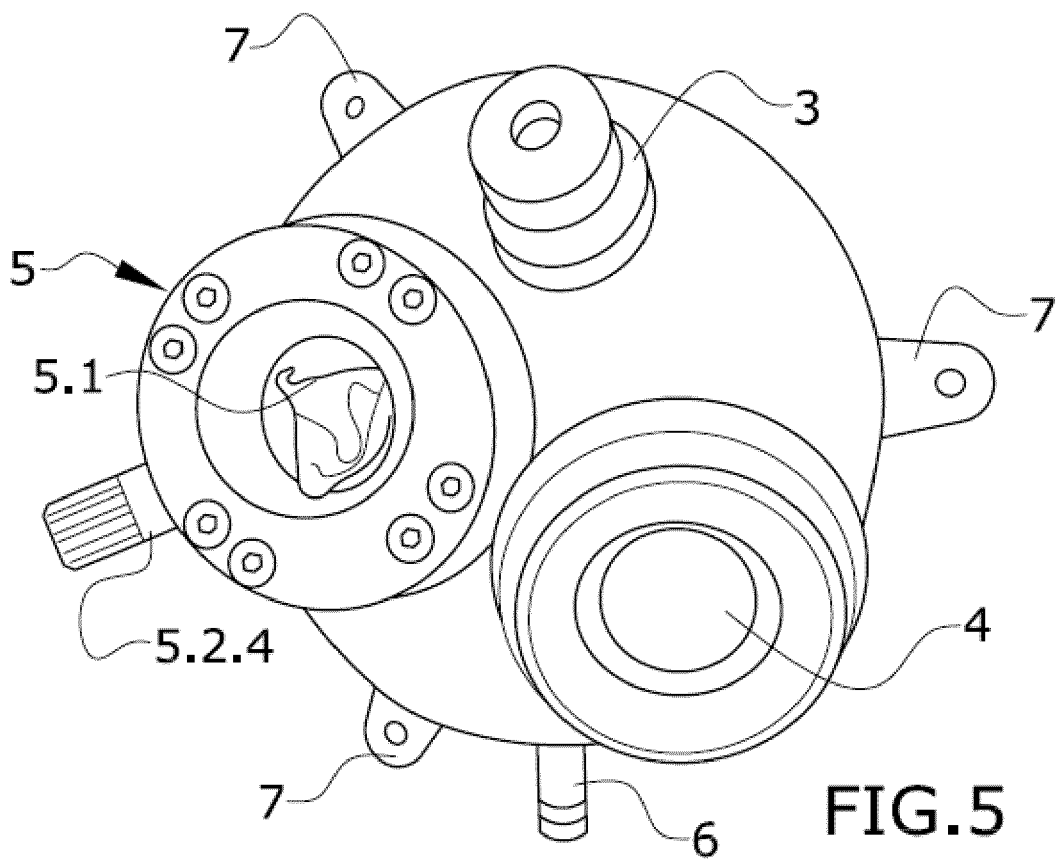
FIG. 5 This figure shows a plan view of a first example of the surgery device as FIG. 4 mounted with additional elements and a sealing system.

FIG. 5 shows the same example of the device (1) of FIG. 4 although additional elements have been mounted in said device (1).

A pneumatic sealing system (5) along with a pump and a three-way valve fixed to the unique cylindrical air distribution system (5.2.4) has been installed on the device (1) by means of inserting said system (5) once mounted intro the main working channel (2) of the device (1). The figure shows the inflatable pad (5.1) of the mentioned pneumatic sealing system (5) deflated. The pneumatic sealing system (5) has been fixed to the body (1.2) of the device (1) by means of screws from the first sealing portion (5.3) through the main body (5.2).

Commercial trocars can be observed mounted on the two secondary working channels (3, 4), being the diameter of the trocar of one of the secondary working channels (3) of 5 mm, thus allowing the passage of instruments of said size. The other secondary working channel (4) has a diameter ranged from 5-12 mm thus allowing the passage of instruments of the same size.

As in FIG. 4, a $CO_2$ input (6) to the cavity and three fixing fins (7) with central holes can be observed in the device (1) of FIG. 1).

Figure 6:
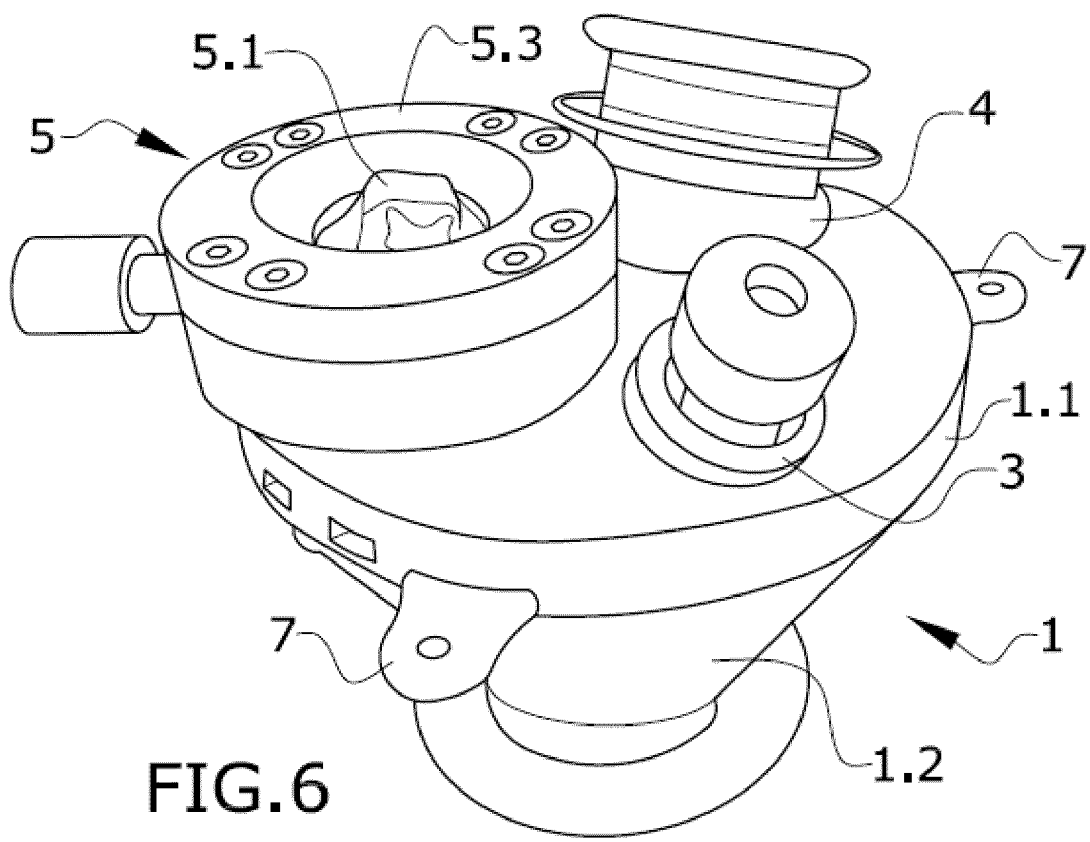
FIG. 6 This figure shows a side view of the first example of the surgery device shown in FIG. 5.

FIG. 6 shows a perspective view of the example of device (1) shown in FIG. 5, wherein a sealing system (5) and two commercial trocars located in the two secondary working channels (3, 4) have been mounted.

As it can be observed, the sealing system (5) has been mounted on the cover (1.1) of the device (1) as well as the retaining means (7), whereas the commercial trocars have been mounted in the two secondary working channels (3, 4).

The body (1.2) of the device (1) has a funnel shape with a neck (1.3) in the bottom part of the mentioned figure, and is made mainly of synthetic polyamide.

Figure 7:
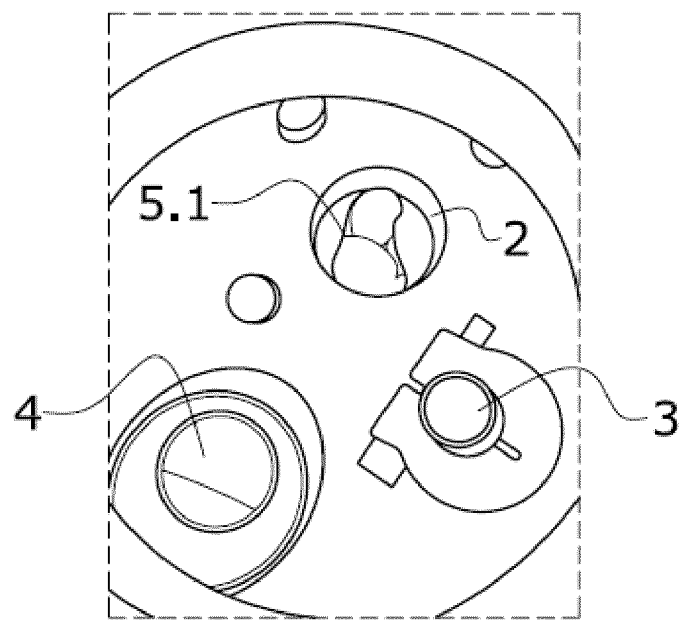
FIG. 7 This figure shows a detailed bottom view of the first example of the surgery device shown in FIG. 5.

FIG. 7 shows a bottom view of the same example of device (1). In this occasion, the main (2) and secondary (3, 4) working channels can be observed from the bottom part of the device (1) when said device (1) is placed as in FIG. 6.

Thus, the main working channel (2) can be observed as going through the whole body (1.2) of the device (1), wherein the inflatable pad (5.1) already inflated is shown.

Additionally, the fixation of the trocars to the secondary working channels (3, 4) is shown. Said channels (3, 4) also pass through the whole body (1.2) of the device (1).

For one of the secondary working channels (4), the trocar is directly attached to the cover (1.1) by means of cyanoacrylate along with a spherical ball joint which is also shown in the figure. This attachment of the trocar is shown in FIG. 7 in the trocar sized 5 mm.

The other secondary working channel (3) has a flexible silicone gel wherein the trocar is embedded. This attachment of the trocar is shown in FIG. 7 in the trocar sized 5-12 mm.

Figure 8:
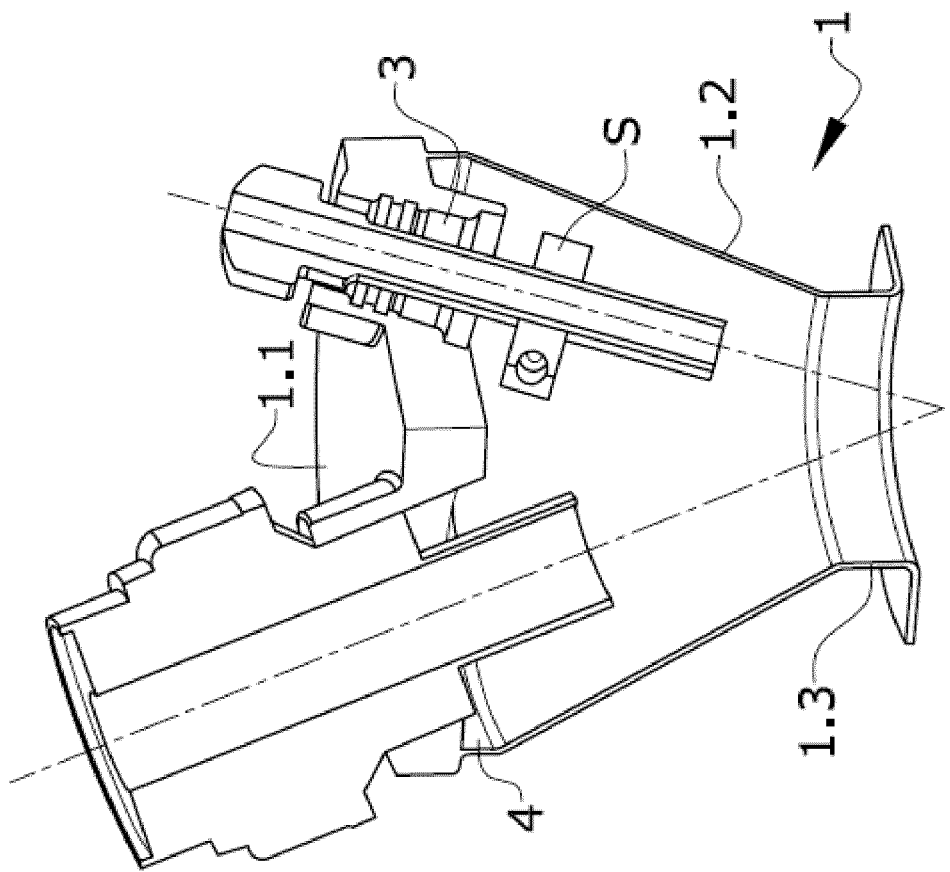
FIG. 8 This figure shows a cross-section view of the example of the surgery device shown in previous figures.

FIG. 8 shows a section of a device (1) wherein trocars have been mounted in the secondary channels (3, 4). Said channels (3, 4) allow a passage of the instruments through the whole body (1.2) of the device (1) from the cover (1.1).

It can be observed how the central axis of the two trocars, coincident with the central axis of the channels (3, 4) is coincident in the central point located in the neck (1.3) of the device (1), which has a funnel shape.

The trocars, as shown, guide the surgery instruments through the channels (3, 4) and allow the proper mobility of said instruments when in use.

It can also be observed in the figure how the trocar mounted in the secondary working channel (3) has a flexible gel for housing and retaining the trocar.

Figure 9:
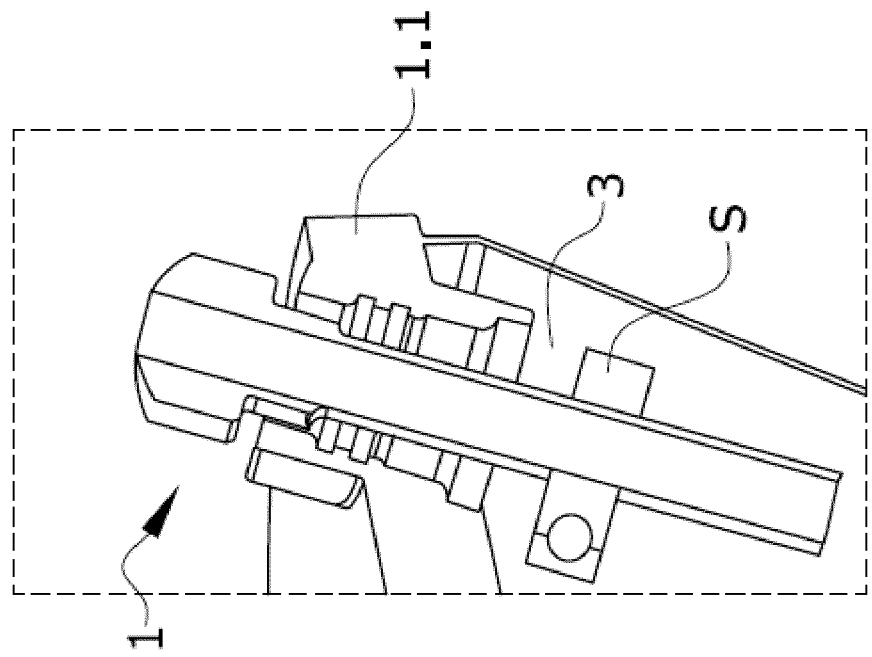
FIG. 9 This figure shows a detail of the view shown in FIG. 8.

FIG. 9 is a detail of FIG. 8, wherein the secondary working channel (3) of the device (1) along with its mounted trocar located on the cover (1.1) is shown.

The trocar has the mentioned a flexible gel of FIG. 8 and the inner part of the cover (1.1) comprises a retention system (S) which avoids the extraction of the trocar. Said system (S) can also be installed in the other secondary working channel (4) for avoiding the movement of the mounted trocar.

Figure 10:
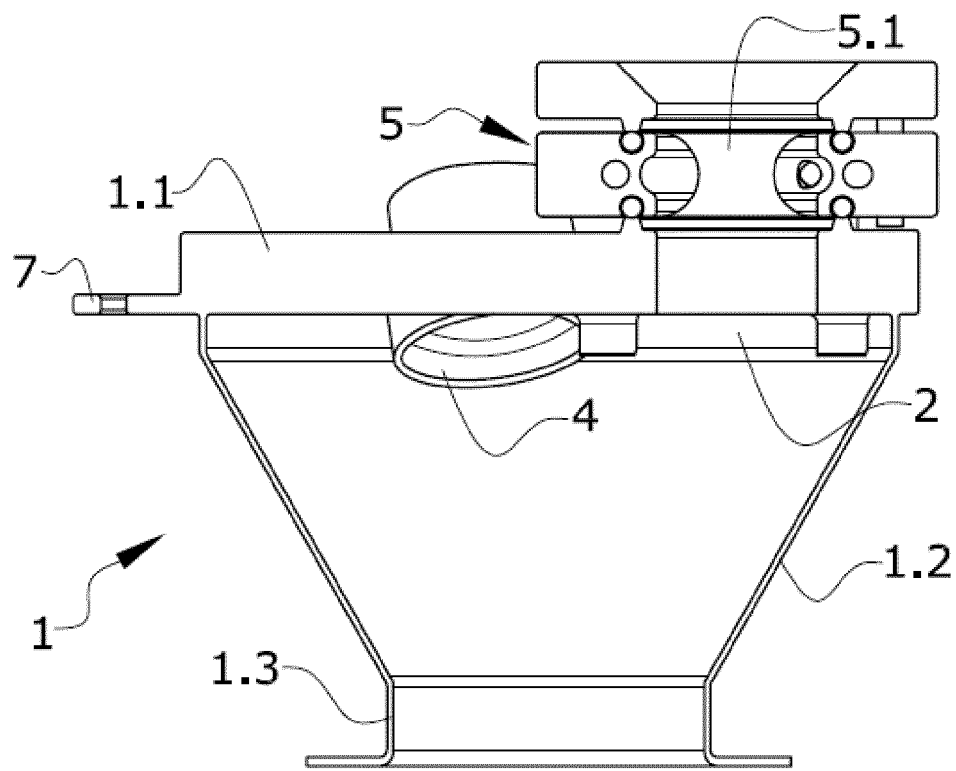
FIG. 10 This figure shows a cross-section side view of the first example of the surgery device shown in previous figures.

FIG. 10 shows a partial transversal section of a device (1) as the one shown in FIG. 6, wherein the device (1) has a sealing system (5) with its corresponding inflatable pad (5.1) mounted on the cover (1.1). The fixing fins (7) are also located in the cover (1.1), manufactured with the same material and integral with said cover (1.1).

The sectioned device (1) allows viewing the main (2) and secondary (4) working channels which pass through the whole body (1.2) of the device (1).

Figure 11:
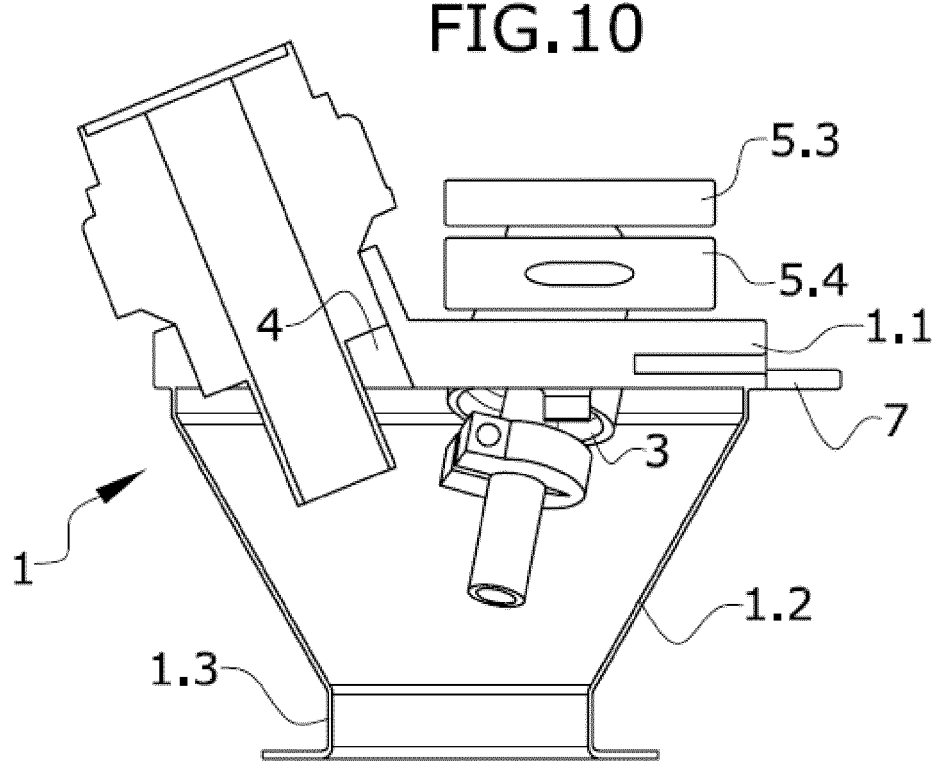
FIG. 11 This figure shows a cross-section view of the view of FIG. 10.

FIG. 11 shows the same device (1) as FIG. 10 from the other opposite side, and wherein trocars have been mounted inside the secondary working channels (3, 4). The guidance parts for the instruments of said trocars can also be seen in the present figure.

Again, the sealing system (5) can be observed mounted on the cover (1.1) of the device (1) and the fixing fins (7) manufactured integral with said cover (1.1).

The invention claimed is:

1. Pneumatic sealing system suitable for being installed in a working channel of a surgery device comprising:
    an inflatable pad inflatable with a fluid and comprising at least one inflatable lobe, such that the inflatable pad directly receives inflating fluid from a fluid distribution system and is configured for exerting pressure on an external element when inflated,
    a main body wherein the inflatable pad is located, the main body comprising:
    a first surface,
    a second surface opposite the first surface,
    an inner passage,
    a fluid distribution system directly connected with the inflatable pad for inflating said inflatable pad through the inner passage,
    a first sealing portion and a second sealing portion, said sealing portions located on the first surface and the second surface respectively of the main body, both sealing portions sealing the inflatable pad, and,
    at least one fixing member for fixing the inflatable pad to the main body.

2. Pneumatic sealing system according to claim 1 further comprising a perimeter recess along the inner passage, and wherein the fluid distribution system comprises:
    at least one fluid inlet, and
    at least one fluid outlet,
wherein the fluid for inflating the inflatable pad flows from the at least one inlet through the perimeter recess and enters the inflatable pad through the at least one fluid outlet.

3. Pneumatic sealing system according to claim 1 wherein the fluid flowing through the fluid distribution system is air, $CO_2$, water or a saline solution.

4. Pneumatic sealing system according claim 1 wherein the fluid distribution system further comprises a luer-lock connection for attaching a 3-way valve.

5. Pneumatic sealing system according to claim 1 wherein the inflatable pad is configured by at least three swelling lobes when inflated which surround the external element.

6. Surgery multichannel device suitable for single incision surgery or natural orifice endoscopic surgery comprising a main working channel, wherein the device further comprises a pneumatic sealing system according to claim 1 installed in the main working channel.

7. Surgery multichannel device according to claim 6 further comprising:
    a cover,
    at least one secondary working channel,
    at least one air input, and
    retention means,
and wherein the main working channel and the at least one secondary working channel are located in the cover.

8. Surgery multichannel device according to claim 6 wherein the main working channel houses a flexible endoscope or rigid optic.

9. Surgery multichannel device according to claim 7 wherein the at least one secondary working channel comprises a trocar attached to it and is configured for housing a rigid instrument.

10. Surgery multichannel device according to claim 9 wherein at least one secondary working channel comprises a flexible gel for housing and retaining the trocar.

11. Surgery multichannel device according to claim 6 comprising two secondary working channels, wherein the secondary working channels each has a central axis and wherein the two central axes converge at one end of the device.

12. Surgery multichannel device according to claim 7 wherein the at least one air input comprises a luer-lock system for connecting a pump.

13. Surgery multichannel device according to claim 6 wherein the main working channel houses rounded-section instruments.

14. Method for installing a pneumatic sealing system according to claim 1 in a surgery multichannel device suitable for single incision surgery or natural orifice endoscopic surgery comprising a main working channel, the method comprising the steps:
    a) fixing the inflatable pad to the main body by means of the at least one fixing member,
    b) adding sealant on the mounting surfaces of the main body and the first and second sealing portions,
    c) locating the first sealing portion and the second sealing portion along with the sealant on the first surface and the second surface of the main body,
    d) compressing the inflatable pad, the main body, the first and second sealing portions and the at least one fixing member together,
    e) inserting the mounted pneumatic sealing system from step d) into the main working channel of the device.

15. Method according to claim 14 wherein step e) comprises resting a portion of the mounted pneumatic sealing system on a cover of the device.

\* \* \* \* \*